United States Patent [19]
Einerhand et al.

[11] Patent Number: 6,140,103
[45] Date of Patent: Oct. 31, 2000

[54] REGULATED PROTEIN EXPRESSION IN STABLY TRANSFECTED MAMMALIAN CELLS

[75] Inventors: Markus Peter Wilhelmus Einerhand, Amsterdam; Domenico Valerio, Leiden, both of Netherlands

[73] Assignee: Introgene B.V., Leiden, Netherlands

[21] Appl. No.: 09/077,444

[22] PCT Filed: Nov. 29, 1996

[86] PCT No.: PCT/NL96/00472

§ 371 Date: Jun. 29, 1998

§ 102(e) Date: Jun. 29, 1998

[87] PCT Pub. No.: WO97/20943

PCT Pub. Date: Jun. 12, 1997

[30] Foreign Application Priority Data

Dec. 1, 1995 [EP] European Pat. Off. .............. 95203307

[51] Int. Cl.[7] .............................. C07H 21/04; C12N 5/10; C12N 7/01; C12N 15/864
[52] U.S. Cl. ..................................... 435/235.1; 435/320.1; 435/325; 435/363; 536/23.1; 536/23.72; 536/24.1
[58] Field of Search .............................. 435/235.1, 320.1, 435/325, 363; 536/23.1, 23.72, 24.1

[56] References Cited

U.S. PATENT DOCUMENTS 5,464,758  11/1995  Gossen et al. .......................... 435/69.1

FOREIGN PATENT DOCUMENTS

| 0 455 424 A2 | 11/1991 | European Pat. Off. . |
| WO 95/13365 | 5/1995 | WIPO . |
| WO 96/40946 | 12/1996 | WIPO . |
| WO 97/00326 | 1/1997 | WIPO . |

OTHER PUBLICATIONS

Chang et al. (1989) Adeno–associated virus p5 promoter contains an adenovirus E1A–inducible element and a binding site for the major late transcription factor. J. Virol. 63:3479–3488, Aug. 1989.

Shi et al. (1991) Transcriptional repression by YY1, a human GLI–Kruppel–related protein, and relief of repression by adenovirus E1A protein. Cell 67:377–388, Oct. 1991.

Antoni et al. (1994) Adeno–associated virus rep protein inhibits human immunodeficiency virus type 1 production in human cells. J. Virol. 65:396–404, Jan. 1991.

Paulweber et al. (1993) The mechanism by which the human apolipoprotein B gene reducer operates involves blocking of transcriptional activation by hepatocyte nuclear factor 3. Mol. Cell. Biol. 13:1534–1546, Mar. 1993.

Frohberg et al. (1991) Characterization of the interaction of plant transcription factors using a bacterial repressor protein. Proc. Natl. Acad. Sci. USA 88:10470–10474, Dec. 1991.

Fields et al. (1996) Fundamental Virology, Third Edition, Lippincott–Raven, Philadelphia, p. 1018, 1996.

Clark et al. (Oct. 1995) Human Gene Therapy, 6:1329–1341.

*Primary Examiner*—Robert A. Schwartzman
*Attorney, Agent, or Firm*—Trask Britt

[57] ABSTRACT

The invention is in the field of recombinant genetic materials, especially for use in gene therapy. Vectors used for transferring additional genetic information to cells in the field of gene therapy are often based on viruses. A group of viruses which has been proposed to use for transfection is the group of parvoviruses, in particular the use of adeno associated virus has been proposed. The invention provides improved methods and means for gene therapy and for preparing products to be used in gene therapy using parvovirus based materials. The invention particularly provides regulated expression of genes under control of the combination of a repressor moiety and an activator moiety, particularly for expression of products which are toxic to the host cell in which they are expressed. In this way it is possible to achieve stable transfection for expression of parvovirus toxic proteins so that amongst others a packaging cell line for producing recombinant parvovirus, in particular adeno associated virus is provided as well as virus produced therewith.

20 Claims, 6 Drawing Sheets

AAV-GENOME STRUCTURE
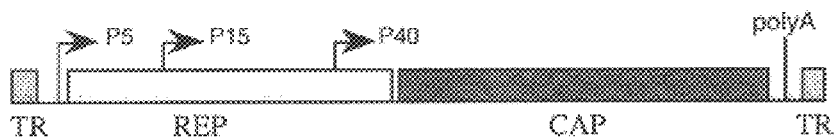
Identified mRNA's and coding regions
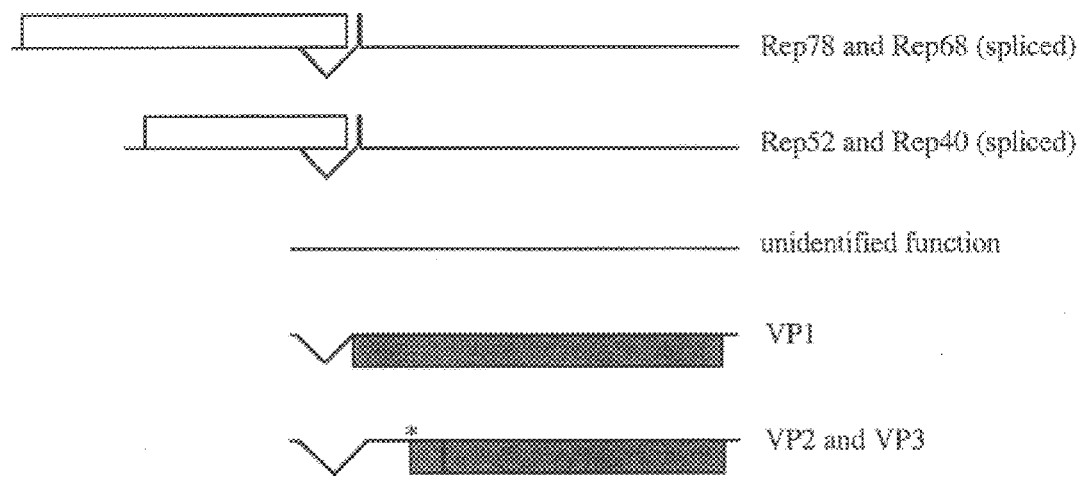
* ACG translation start of VP2
Fig. 1

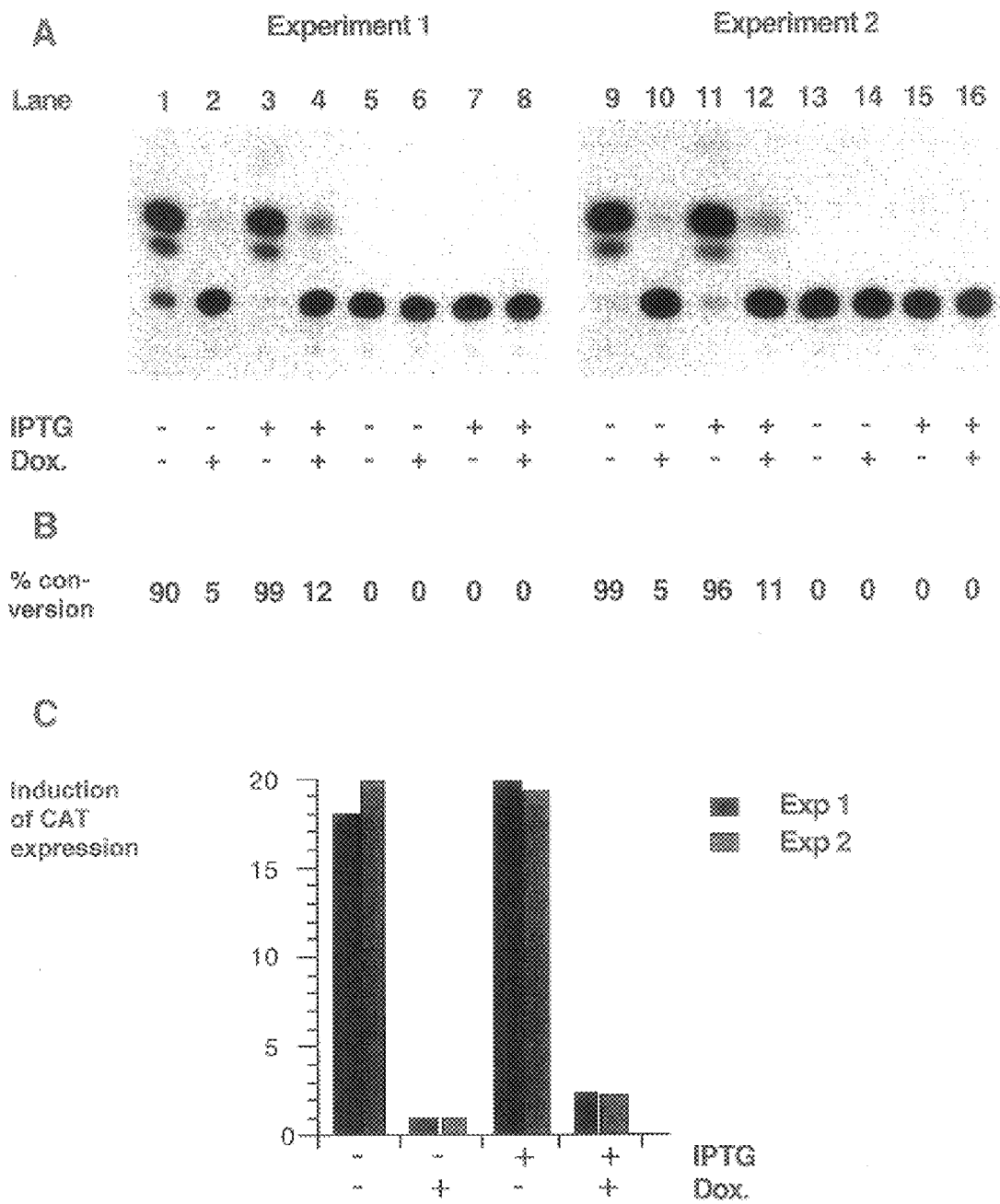
Fig 6. Efficient silencing by a transcription unit controlled by a regulatable repressor and activator

REGULATED PROTEIN EXPRESSION IN STABLY TRANSFECTED MAMMALIAN CELLS

The present invention relates to recombinant DNA molecules encoding products of interest, as well as to methods employing said molecules. In particular, it relates to recombinant DNA molecules capable of regulated expression of one or more genes in a host cell. In particular, the invention relates to expression of products which are in some way toxic when expressed in a host cell. A good example of such a product or products are the products of non-structural genes of parvoviruses (PV). Because these products are toxic to their host cells it is not feasible to arrange for constitutive expression of said products in host cells.

High level PV-protein expression in stably transfected mammalian cells is very often an elusive goal in trying to make host cells express PV-proteins genes introduced therein by recombinant DNA technology. For instance, high levels of PV-protein synthesis in human cells are of importance for the production of packaging cells for recombinant PV vectors. In such packaging cells, the recombinant PV. vector DNA is replicated and packaged into PV-capsids when PV-proteins are supplied in trans by the packaging cell.

The parvovirus Adeno-Associated Virus (AAV) is a non-pathogenic human parvovirus (reviewed in [1, 2]). The virus replicates to a single stranded DNA of approximately 4.6 kb. Both the plus and the minus strand are packaged and infectious. Efficient replication of AAV requires the co-infection of the cell by a helper virus such as Adenovirus or Herpes Simplex Virus. In the absence of a helper virus, no substantial replication of AAV is observed. AAV is therefore also classified as a "Dependovirus". When no helper virus is present, the AAV genome integrates into the host cell genome.

The wild-type virus has a strong preference (70%) for an integration site on the long arm of chromosome 19 (19 q13.3) [3-5].

Following integration, the expression of the virus genes is not detectable. The integrated provirus replicates as a normal part of the host cell genome upon division of the transduced cell and ends up in both daughter cells. This stage of the virus life cycle is known as the latent stage. This latent stage is very stable, but can be interrupted upon infection of the transduced cell by a helper virus. Following infection by the helpervirus, AAV is excised from the host cell genome, expresses its genes and starts to replicate. During the early phase of this lytic cycle, the REP-genes are expressed. After approximately 16 hours, the capsid proteins VP1, VP2 en VP3 are expressed and the replicated virus is packaged into virions (structure of the AAV-genome and its genes are depicted in FIG. 1). The virions accumulate in the nucleus of the cell and are released when the cell lyses as a result of the accumulation of AAV and the helpervirus.

The AAV-genome consists of two genes rep and cap (FIG. 1). Three promoters (P5, P19 and P40) drive the synthesis of mRNAs coding for 4 Rep-proteins (Rep78, Rep68, Rep52 and Rep40) and three capsid proteins (VP1, VP2 and VP3). Both the Rep and the VP-proteins are encoded in overlapping reading frames. Therefore the Rep proteins and also the VP-proteins share a common carboxy-terminal end but differ in their N-termini. The AAV-genome is flanked on both sides by a 145 bp sequence, called the Inverted Terminal Repeat (ITR). The ITR contains all information required in cis for replication, packaging and integration of the AAV-genome. During a productive infection, the P5-promoter is activated first and directs the production of Rep78 and Rep68. These proteins are essential for AAV-replication and trans regulation of viral genes. The large Rep-proteins activate the P19 and the P40 promoter. In a latent infection, however, Rep78 and Rep68 downregulate expression of the P5 promoter and help to maintain the latency of AAV (for a review see1). The smaller Rep-proteins, Rep52 and Rep40 are encoded by transcripts from the P19 promoter and are important for the formation of infectious virus [6]. The P40 promoter is the last promoter to become activated and the expression follows the expression of the late genes of the helper adenovirus. Via alternative splicing, different mRNA's are produced, coding for the structural proteins VP1, VP2 en VP3. VP2 and VP3 are translated from the same messenger, whereby VP2 starts at an upstream ACG. A mature AAV virion consists of 5% VP1, 5% VP2 and 90% VP3 [7].

The first recombinant AAV vectors were made by replacing sequences from the rep or the cap gene by the sequences of interest [8-10]. The vector genome was packaged by co-transfecting into adenovirus infected cells a plasmid containing the vector with either a plasmid containing the missing AAV-gene or a recombinant AAV-genome that was too large to be packaged by an insertion of lambda phage DNA [8-10]. Recombinant virus that was produced in this way was always contaminated with wild-type AAV (ranging from 10–50% compared to the recombinant titer). This was presumably due to recombination between the two co-transfected plasmids which contained a substantial region of overlap, or by loss of the lambda DNA sequence. The contaminating wild-type AAV resulted in a further amplification of the rAAV upon infection of a new batch of adenovirus infected cells. This led to higher rAAV-titers but also caused amplification of the contaminating wild-type AAV [8-10].

To circumvent the production of wild-type AAV, a packaging plasmid was constructed that contained no overlap with the vector plasmid [11]. With this packaging plasmid, it is possible to generate rAAV virus stock which is free of detectable amounts of wild-type AAV and at the same time enabling the production of 0.1 to 1 rAAV particles per cell [11]. This packaging system or analogous systems derived therefrom are currently standardly used by most laboratories. Although this is the method of choice at present, the method is far from optimal and cannot easily be scaled up to allow for "industrial" production of rAAV vectors. Plasmid transfections are inherently inefficient and difficult to standardize or to scale up. This is even more true for co-transfections. In addition, whereas the wild-type virus replicates to $10^3$–$10^4$ particles per cell, the yield of rAAV in a typical rAAV-production (01–1 particles per cell) is very low with the current methods [11, 12]. This low yield makes purification of the rAAV a difficult task to undertake. The production problems pose a real technological obstacle for the further development of AAV-vector technology for gene therapy purposes. There is clearly a great need for an efficient but simple method for the production of rAAV. The most convenient packaging system would be in vitro packaging of rAAV by purified recombinantly produced AAV-proteins. A practical alternative is the generation of a packaging cell line for rAAV where the packaging cell line supplies in trans the required AAV and helper virus proteins for the production of rAAV. The specific recombinant AAV producing cell lines can be generated by stably transfecting a plasmid containing the recombinant AAV into the packaging cells. The present invention is useful for both the in vitro packaging strategy and the packaging cell line strategy.

Packaging cell lines are currently the most efficient way in which retrovirus and adenovirus vectors are produced for therapeutical purposes such as gene therapy [13, 14]. Virus protein production for the in vitro packaging on an industrial scale is currently employed for Lambda phages. The currently available packaging cell lines for retrovirus and adenovirus vectors constitutively produce the in trans required virus proteins [15–21]. Mammalian cells, useful for efficient packaging of rAAV or the production of AAV proteins, are not available. Recombinant AAV packaging cell lines require that production of the in trans required AAV-proteins are present in the cells only during the production phase of the rAAV vector. Constitutive expression is not desired for two reasons: 1) rescue and replication of the vector DNA prior to production would interfere with the growth and the stability of the cell line and 2) specifically, Rep-proteins are toxic to cells even in the absence of a recombinant AAV vector. The latter is largely due to the well documented, but as yet not characterized, anti-proliferative effect of the large Rep proteins [22, 23]. Rep78 and Rep68 repress both cellular and viral promoters in transient assays [24, 25]. Upon stable transfection, the large Rep proteins inhibit cell proliferation 22, 23. The mechanism is not well understood. It is possible that the observed inhibition of mRNA transcription and translation represses crucial cellular genes [26-28]. On the other hand is it possible that the large Rep-proteins inhibit DNA replication directly [24, 29, 30]A. Considering the pleiotropic effect of Rep-protein expression on cells, it is possible that both effects play a role in the anti-proliferative effect of the large Rep-proteins.

It is not possible to make stable cell lines expressing the large Rep-proteins constitutively (our own unpublished results). Following substitution of the P5 promoter with an inducible promoter such as the methallothionine promoter [22] or the steroid inducible Mouse Mammary Tumor Virus (MMTV) long terminal repeat (LTR) promoter, [23] it was possible to isolate out of a large number of clones respectively one and two clones that inducibly expressed Rep78. Rep52 was expressed constitutively in two of the three clones, whereas Rep68 en Rep40 which are translated from the spliced mRNAs were not detectable [22, 2]. Although the clones were able to functionally produce Rep78 and Rep52, the level was too low for the replication and packaging of recombinant AAV [22, 23]. Furthermore, the percentage of clones expressing Rep78 was very low. Thus, there was a strong selection against a high level of rep expression.

Recently, Clark et al. [30b] reported the generation of dedicated cell lines capable of producing specific rAAV vectors upon adenovirus infection.

This was achieved by transfecting a single, covalently closed, plasmid construct, carrying a rAAV genome, a selection markergene and an AAV-packaging genome. On the other hand, stable transfection of only the packaging construct and a selectable markergene resulted in cell lines that, after transfection of a rAAV construct, were capable of replicating rAAV but not packaging rAAV. Thus, this method can not be used to generate universal packaging cell lines for the production of different rAAV vectors.

In trying to solve the problem mentioned above, we have now succeeded to provide for regulated expression of recombinant DNA molecules in host cells by a method in which the expression can be essentially completely switched off. While we have found this unexpected means in a recombinant andenovirus associated virus vector system, it will be clear to the person skilled in the art that this phenomenon will be applicable in a much broader field, at least to other parvovirus vector systems, if not generally applicable to mammalian or even eukaryotic cells.

The invention thus provides a recombinant DNA molecule, comprising a gene, which gene is under the control of a combination of an inducible repressor and an inducible transactivator. We have found that by putting the gene to be expressed under this control regimen, whereby at least an inducible repressor function and a separate inducible activator function are present upstream of (and functionally linked to) the gene of interest, that expression can be essentially completely suppressed by inducing the repression and not inducing the activator. If the activator is a modulator, in that it represses in the one situation and activates in the other, it is clear that the modulator should be in the repression situation. The same is, of course true, if the repressor is also a modulator. It is important only that a repression functionality is present at the same time as a non-functional activator in the "switched off" state and a non-functional repressor and a functional activator functionality in the "switched on" state. This may, thus, be arrived at by any combination of the two, either repressor-activator, modulator-modulator, modulator-repressor or modulator activator. Not only is the expression essentially completely switched off in the "off" state, but also the expression levels in the "on" state are unexpectedly high.

The invention is particularly useful for the expression of genes of which the product is toxic for cells expressing said product. There are, of course, many known inducible repressors and/or activators, some of which may be promoters and others being parts of a DNA molecule upstream of a promoter, all of which may be used according to the present invention. The term inducible is meant to include all such promoters, activators or repressors which respond to the presence or absence of a signal, such as the presence of a chemical substance or a change of temperature, by either improving transcription or reducing transcription. The choice that has to be made is that both functionalities (repressor and activator) together result in an essentially complete "switch-off" and an enhanced "switched-on" state. A number of preferred combinations is given herein below. One such a combination comprises at least one transactivator sequence which is a binding site for a tetracycline repressor, preferably one whereby the binding site is derived from tn10 described herein below.

Another such a preferred embodiment comprises a recombinant DNA molecule whereby at least one inducible repressor sequence is a binding site for a YY1 repressor, or whereby at least one inducible repressor is a binding site for a major late transcription factor (MTLF), or whereby at least one inducible repressor is derived from an adeno-associated virus p5 promoter, all described below.

The invented molecules are preferably used to express parvovirus gene products. A preferred embodiment, therefore, comprises a recombinant DNA molecule whereby the gene encodes at least a specific part of a Parvovirus protein and/or a recombinant DNA molecule whereby the gene is a Parvovirus non-structural gene, preferably an adeno-associated virus rep gene.

Using the recombinant DNA molecules according to the invention, cells can be stably transfected therewith. Such cells are also a part of the present invention, especially such cells which have been immortalized and which are of mammalian origin.

One of the goals of the present invention is providing better means and methods for gene therapy for which the most suitable cells to use in prodcution of means for gene therapy are mammalian cells. They are also the natural host for the viruses which are preferred according to the present invention. The cells according to the invention, which are to be used as production facilities for recombinant virus protein, particles or virions, or which are packaging cell lines need to be capable of induced expression and inducible repression of the gene comprised in the recombinant DNA molecule.

When the cells are used for packaging or production of recombinant adenovirus associated virus particles they should, preferably, at least be capable of inducible expression and repression of Rep78/Rep68 or derivatives thereof, of an adeno associated virus.

Cell lines to be used as production facility for recombinant parvovirus production, preferably rAAV, should comprise packaging cells according to the invention which have been provided with at least one additional recombinant nucleic acid molecule to be packaged into a parvovirus, preferably rAAV, which additional nucleic acid should comprise at least a gene of interest, flanked by parvovirus inverted terminal repeats conveying in cis the required sequence information for rescue, replication, packaging and integration of the rAAV vector.

Preferred is a cell line whereby the materials necessary for the production of virus particles are present in the genetic material of the packaging cell or on the additional recombinant nucleic acid, but not on both. The present invention also provides methods for producing recombinant parvovirus comprising culturing a cell line, according to the invention, in a suitable culture medium and harvesting recombinant parvoviruses from said culture, as well as that it comprises recombinant parvovirus obtainable by such a method.

The present invention further provides a cell line expressing in a regulated fashion Rep78 and Rep68, useful for the production and purification of AAV-proteins and the production of a rAAV packaging cell line. It further discloses the identification of sequences in the AAV p5 promoter that, combined with regulated promoter elements or alone, facilitate regulated expression of Rep78 and Rep68 in stably transfected mammalian cells. The present invention further discloses methods for the generation of such cell lines expressing the AAV-coding regions in mammalian cells useful for the generation of rAAV-packaging cells.

In one embodiment of the invention, a cell line expressing high levels of Rep78 and Rep68 in a regulated fashion is provided.

In a further embodiment, methods to obtain regulated AAV-protein synthesis in mammalian cells useful for the generation of rAAV-packaging cell lines are provided.

A further embodiment of the invention comprises methods to improve the quality of rAAV-preparations by reducing the amount of wild-type AAV produced and methods to improve the overall yield of rAAV per cell by separating the AAV-transcription units and placing them on different constructs.

It will be understood that by the term "recombinant AAV packaging cell" a cell line is meant which provides in trans required AAV-proteins necessary for the replication and/or packaging of modified wild-type or recombinant AAV genomes. The in trans required proteins are provided either in a constitutive fashion or in a regulated fashion.

As used herein, the term "functional levels of parvovirus protein expression" refers to levels of expression sufficient for replication and/or packaging of recombinant or modified wild-type parvovirus genomes.

It is understood that the term "regulated expression" is intended to mean expression levels which can be altered either by manipulating the cell's environment or by infecting the cells with a virus such as adenovirus or herpes simplex virus.

It will be further understood, as more or less stated before, that the term "regulated promoter" means a DNA sequence, preferably a promoter, which enables a linked gene to be expressed at levels that can be modified by changing the cell's environment, for instance by the addition or removal of compounds to the medium in which the cells are grown.

The system of repression, combined with activation, may be used in in vivo settings as well, whereby switching on and off of the gene is achieved by administration of an inducing agent.

DESCRIPTION OF THE DRAWINGS

FIG. 1 depicts the structure and the genome organization of wtAAV.

FIGS. 6A–6C depicts two experiments in which efficient silencing of CAT-expression is observed in the uninduced state from a transcription unit governed by a regulatable transactivator and repressor. FIG. 6A shows an autoradiogram of a CAT-activity analysis, lanes 1 to 4 and lanes 9 to 12 depict CAT-activity in ptet(o)OPCAT;pCMVLacI, pBluescript SK+, pCMVLacZ DNA transfected cells. Lanes 5 to 8 and 13 to 16 depict CAT-activity cells from untransfected control cultures. FIG. 6B shows the measured chloroamphenicol conversion. FIG. 6C shows the induction of CAT-activity in lanes 1 to 4, and lanes 9 to 12, relative to the CAT-activity in lanes 2 and 10, respectively.

DETAILED DESCRIPTION OF THE INVENTION

Figure 2:
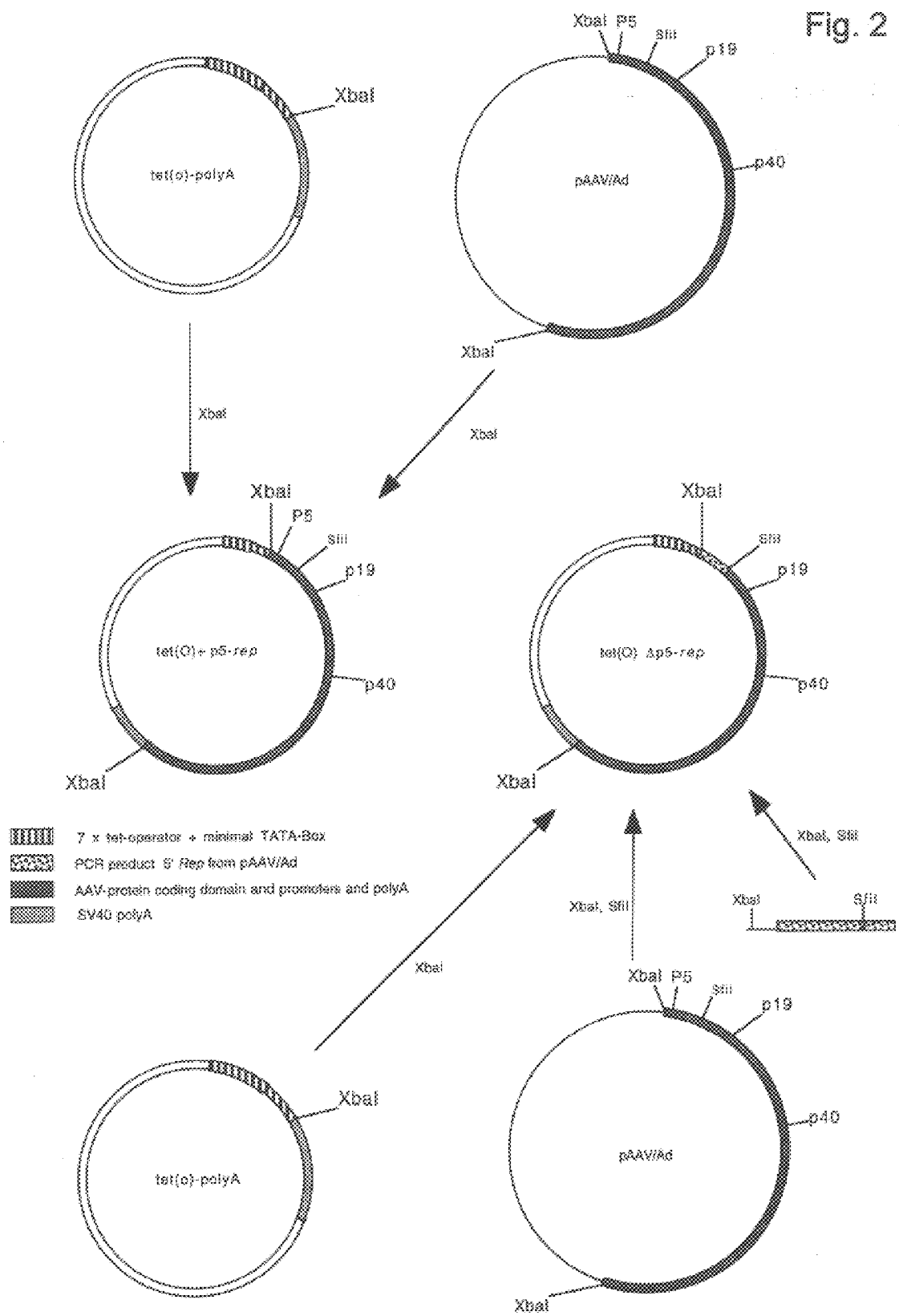
FIG. 2 depicts the construction of tet(O)+p5-rep and tet(O) ΔP5-rep

The present invention is, in one aspect, based on the discovery of sequences that enable the efficient production of stable cell lines, expressing in a regulated fashion, high levels of Rep78 and Rep68. As noted above, it has been shown to be possible to obtain stable clones expressing the Rep78 protein in a regulated fashion. However, the frequency with which such clones are found and, more importantly, the level of regulated Rep78 expression, is very low. This has severely limited the application and the development of packaging cell lines for rAAV. The present invention, for the first time, describes the generation of efficient packaging cell lines for the production of recombinant AAV.

The classical inducible eukaryotic promoters, like, for instance, the mouse methallothionine promoter or the mouse mammary-tumor virus long terminal repeat promoter, respond to heavy metals, heat shock or hormones [31-38]. Furthermore, the human immunodeficiency virus (HIV) long terminal repeat promoter can be induced by the HIV transactivator protein TAT or by the adenovirus E1A protein. An inducible expression system, based on HIV promoter induction by TAT, has been described in patent application EP 0 455 424 and expression of AAV rep proteins, driven by the HIV promoter, was suggested in patent application WO 95/13365. However, all these inducible promoters are, in principle, not ideally suited to inducibly express (toxic) genes, since the promoters are not completely silent in the uninduced state[32] and/or because the inducing principle induces pleiotropic effects in the target cells [39]. A new generation of regulated promoters has adapted parts from bacterial transcription units for use in eukaryotic cells [40-47]. These artificial transcription units are adapted from the lac repressor-operator-inducer system or the TN10-specific tetracycline resistance operon from E. coli. Three different systems have been described: i) the prevention of transcription initiation by well placed repressor-operator complexes on the promoter [40-42, 46]; or ii) in blocking of RNA-polymerase II during elongation by a repressor-operator complex [43, 46]; or iii) the activation of a minimal TATA-box, replenished with operator sequences which can be recognized by an artificial transactivator (tA), wherein the tA consists of the operator binding component derived from the lac-repressor or the tetracycline repressor and the transcription activating domain from VP16, a Herpes Simplex Virus encoded transcription activator [44, 45, 47]. Binding of the tA to the operator sequences can be effectively inhibited with specific compounds, i.e. IPTG for tA, based on the lac-repressor operator binding domain, and tetracycline or tetracycline-related compounds for tA, based on the tetracycline-repressor operator binding domain.

Specifically, the latter system, where a minimal promoter is combined with operator sequences from the tet-repressor, is suitable for the regulated expression of foreign genes. Since, in eukaryotic cells, no functional transactivating proteins bind to the tet-operator sequences, these promoters are practically inactive in the presence of low concentrations of tetracycline or related compounds such as doxycycline [47, 48]. Similarly, suitable expression patterns can be obtained with the system utilizing a tA comprising the operator binding component of the lac-repressor. However, the utility of lac-repressor/operator based systems in mammalian cells is limited, because the inducer compound β-D-thiogalactopyranoside (IPTG), despite its rapid uptake and intracellular stability, acts rather slowly and inefficient. Consequently, such systems give only moderate expression induction (47). Stable cell lines exist that constitutively express the tetracycline-repressor VP16 fusion gene (tA). Therefore, in one embodiment of the invention, the AAV rep gene is placed downstream from the tet operon and this construct is introduced into tA-expressing cells. Tetracycline, or related compounds, are present in the medium during cell expansion. AAV rep expression can be induced by removal of said compounds from the culture.

Even though tetracycline and many tetracycline derivatives are nontoxic to eukaryotic cells at the low concentration required to abolish gene expression, their continuous presence is suboptimal in a variety of experimental and industrial setups; for example, in the breeding of transgenic animals, in gene therapy or in large volume bioreactors, where, for full activation of gene expression, the tetracycline or derivative needs to be washed out rigorously. For these purposes, an inducing effector substance would be preferred over an inhibiting compound and, as such, a modified tA was developed (Gossen et al., Science 268 (1995):1766–1769). Several mutations in the Tet-repressor resulted in reversal of the binding characteristics of the repressor protein (binding in the presence of tetracycline and no-binding in its absence). This new protein is referred to as a reverse Tet repressor (rTetR). A reverse tetracycline-controlled activator (rtTA), in which rTetR was fused to VP16, was developed. Cell lines, expressing the rtTA, were generated and can be used to express tet-operon controlled transcription units upon induction with tetracycline or tetracycline derivatives (Gossen et al., Science 268(1995):1766–1769). Therefore, in another embodiment of the present invention, the AAV rep gene, cloned downstream from the tet operon, is introduced into rtTA-expressing cells and AAV rep expression can be induced by the addition of tetracycline or related compounds to the medium.

The invention is illustrated by the following non-limiting examples, wherein the following materials and methods were employed. The entire disclosures of each of the literature references cited hereinafter are incorporated by reference herein.

EXAMPLE 1

Ligation of the AAV-genome lacking the flanking ITR to a regulated promoter.

We have used a HeLa cell line HtTA expressing the tA constitutively [47] to test for regulated rep expression from tet(O)-rep gene constructs. To this end, we cloned a 4.3 kb XbaI fragment derived from pAAV/Ad [11] (a kind gift from Dr. R.J. Samulski) containing the entire rep and cap coding domain in the XbaI site immediately downstream of the tet(O) (FIG. 2). In this construct, designated tet(O)+p5-rep, the tet(O) is situated upstream of a -68 bp p5-promoter (measured from the first base of the TATA-Box). To completely substitute the p5-promoter for the tet(O), we had to perform a PCR reaction, due to the absence of suitable restriction sites. The upstream primer was 5'-ATTAATCTAGACTAGTCGCGCAGCCGCCATGCC-GGGG-3' (SEQ. ID NO:1) and the downstream primer was 5'-TGTGGAAGTAGCTCTCTCCC-3' (SEQ. ID NO:2). The PCR reaction was performed on pAAV/Ad with pfu™ (Stratagene) using the buffer and the reaction conditions recommended by the manufacturer. The final construct, tet(O) Δp5-rep, was generated by digesting the 299 bp PCR product with SfiI and XbaI and ligating the resulting 248 bp fragment in a three part ligation with a 3.95 kb SfiI-XbaI fragment from pAAV/Ad into the XbaI site immediately downstream of the tet(O) construct. The amplified part of the construct was checked by sequencing and found to be as expected.

EXAMPLE 2

Expression of rep and cap from these plasmids.

Figure 3:
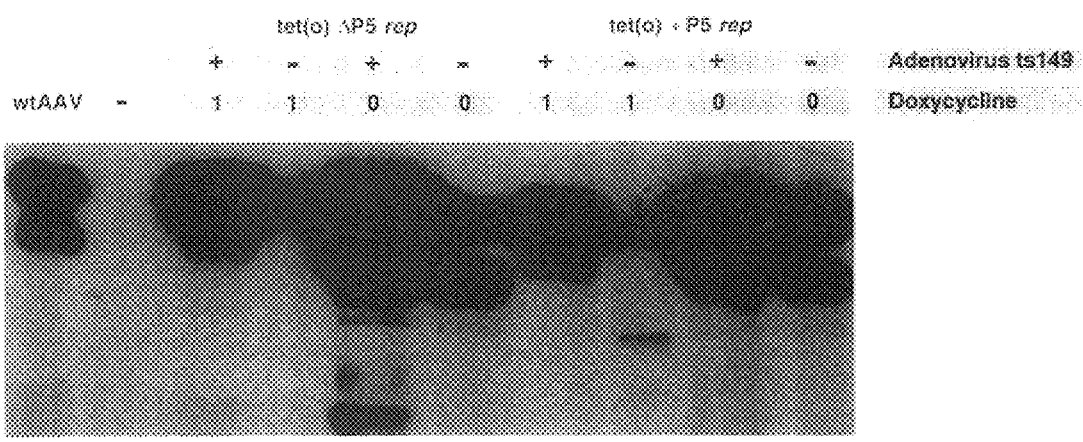
FIG. 3 depicts regulated expression of Rep78 and Rep68 from tet(O)+p5-rep and tet(O) ΔP5-rep in transiently transfected HtTA cells.

In order to test the expression capabilities of the recombinant AAV packaging constructs, it was necessary to determine the activities of the various promoters. For this purpose, the tet(O) Δp5-rep and the tet(O)+p5-rep were transfected into HtTA-cells in the presence or absence of (1 μg/ml) doxycycline and in the absence or presence of adenovirus ts149 (moi=20). Protein was extracted after two days and western blotted. The filters were incubated with the Rep78, Rep68 specific monoclonal antibody 7B7 (a kind gift of Dr. R. J. Samulski) (FIG. 3). Both the tet(O) Δp5-rep and the tet(O)+p5-rep constructs express Rep78 and Rep68 in a doxycycline regulated fashion in HtTA cells. Both the tet(O) ΔpS-rep promoter and the tet(O)+p5-rep promoter are upregulated upon adenovirus infection. Rep78 and Rep68 expression in the uninduced state (i.e. with doxycycline and without adenovirus) is markedly reduced with the tet(O)+p5-rep, as compared to Rep78 and Rep68 expression from the tet(O) Δp5-rep construct under the same conditions. These results prove i) that it is possible to obtain regulated expression Rep78/Rep68 using the artifical tet-operon. ii) that adenovirus infection up-regulates expression from the rep-gene in both constructs. This is possibly due to a direct effect on the tet(O) and the minimal TATA-Box, or due to an adenovirus responsive element (an enhancer) in the AAV-genome. Another possible mechanism is an adenovirus induced enhanced translation of Rep78/Rep68 specific mRNA in adenovirus infected cells. iii) In the tet(O)+p5-rep construct the major late transcription factor (MTLF) site and the two YY1-sites in the P5 promoter are likely to mediate at least part of the observed down-regulation of Rep78 and Rep68 expression from tet(O) +P5-rep in the uninduced state and the up-regulation of Rep78 and Rep68 expression from tet(O) +P5-rep in adenovirus infected HtTA cells.

Figure 4:
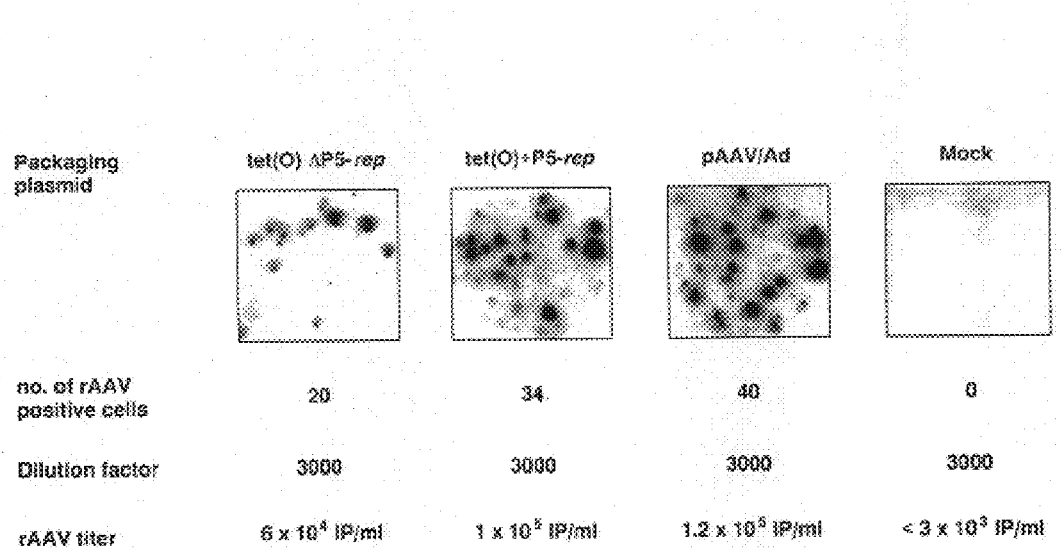
FIG. 4 depicts the use of tet(O)+P5-rep and tet(O) ΔP5-rep as packaging constructs for the production of the recombinant AAV IG-CFT. The packaging plasmid pAAV/Ad served as a positive control for the assay and Adenovirus-infected HtTA cells served as a negative control for the assay.

To determine whether the rep-gene expression was functional, the constructs were used to produce recombinant AAV. For this purpose the constructs were co-transfected with a plasmid pIG-CFT, carrying a recombinant AAV vector 49 into adenovirus ts149 (moi=20) infected HtTA cells. After incubation at 39° C. and 10% $CO_2$ for three days, the cells and the culture supernatant were collected and subjected to three freeze thaw cycles, as described in [49]. Cell debri was removed by centrifugation (1200 rpm, rt) and residual adenovirus ts149 was heat inactivated (1 hour, 56° C.). Recombinant AAV was titrated in a replication center assay (RCA) by serial dilution of the recombinant AAV stock on adenovirus ts149 and wtAAV infected 293 cells[20], as described in [49]. This assay takes advantage of the fact that recombinant AAV-DNA is replicated to very large amounts in wtAAV and adenovirus infected 293 cells. After one day, the vector DNA accumulation in the nucleus of transduced cells is large enough to allow the detection of individual infected cells following hybridization with a vector specific probe. For this purpose, the cells were collected in PBS-EDTA (5 mM) after one day and single cell suspensions were transferred to a hybond N+nylon membrane. After processing of the filter and hybridization with a neo-probe (1002 bp SmaI fragment), individual spots point out cells transduced by the recombinant AAV-vector. Using the RCA, the tet(O) Δp5-rep packaging construct produced about 20 spots which, adjusted for the dilution, corresponded to a titer of $6\times10^4$ Infectious Particles (IP) per ml, whereas the tet(O)+P5-rep packaging construct produced about 34 spots corresponding to a titer of $1.0\times1.0^5$ IP per ml (FIG. 4). Thus, the AAV-protein coding domain is functional in both constructs.

EXAMPLE 3

Stable cell lines expressing regulated high levels Rep78 and Rep68.

It has previously been shown that the adeno-associated virus P5 promoter contains a motif centered at −60 and +1, relative to its initiation site that mediates transactivation by the 13S E1A protein. A cellular factor, YY1, that binds to the motif was identified, and its cDNA was cloned. YY1 is a 414-amino-acid zinc finger protein that represses transcription when bound upstream of heterologous basal promoters; E1A-proteins relieve the repression and activate transcription through YY1 [50].

Figure 5:
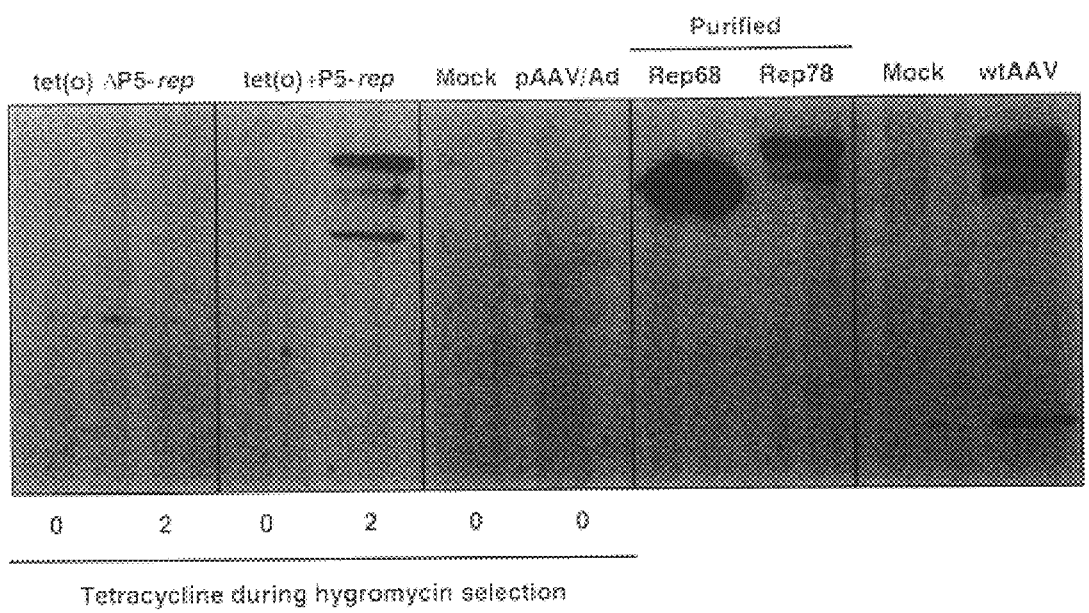
FIG. 5 depicts regulated expression of Rep78 and Rep68 from tet(O)+p5-rep and tet(O) ΔP5-rep in stably transfected HtTA cells.

To determine whether stable cell lines expressing high levels of Rep78 and Rep68 in a regulated fashion could be generated, we performed co-transfections in HtTA cells of tet(O) Δp5-rep or the tet(O)+P5-rep with plasmid pX343 containing a hygromycin B resistance gene under transcriptional control of the SV40 promoter in a ratio of 10:1 respectively Transfections were done in the absence or presence of 2 μg/ml tetracycline. Two days after transfection, the medium was replaced by a medium containing 400 μg/ml Hygromycine B with or without 2 μg/ml tetracycline. This selection medium was refreshed every 3 to 4 days. After two weeks, the colonies in the dishes were trypsinised, seeded in medium without tetracyline and infected with adenovirus ts149 (moi=20). After two days, the cells were collected and total protein was western blotted. Rep-protein expression was analyzed using the Rep78/Rep68 specific monoclonal antibody 7B7. In untreated cells (lane HtTA) and in pBluescript transfected HtTA cells (pBlue), no Rep-specific bands are detected. In the positive control lane, HtTA infected with wtAAV-2, Rep78 and Rep68 are easily detected. Rep68 runs as a double band in SDS-page (M.E. unpublished results). Purified Rep78 and Rep68 protein (kindly provided by Dr. Nick Muzyczka) in the lanes marked as Rep78; Rep68 served as size markers for the respective proteins. When pAAV/Ad [11] was transfected or when the tet(O) Δp5-rep construct was transfected, no Rep78 or Rep68 could be detected in the adenovirus infected pools (FIG. 5).

Thus, constructs carrying only the p5-promotor (pAAV/Ad) as functional element driving expression of Rep7B and Rep68 are much less efficient in generating stable cell lines expressing Rep78/Rep68 in a regulatable fashion than combinations of a regulatable activator with the p5-promotor (tet(O)+p5-rep).

This complies with the notion that even low levels of Rep78 and Rep68 inhibit cell growth. The tet(O)+p5-rep construct, in contrast, does express significant amounts of Rep78 and Rep68 in a regulated fashion (FIG. 5). Pools generated in the presence of tetracycline, when the tet(O) is inactive, express Rep78 and Rep68 upon removal of the tetracycline from the medium. However, when pools were generated in the absence of tetracycline, when the tet(O) is active, no expression of Rep78 and Rep68 can be detected. These results indicate the presence of sequences in the p5 promoter that down-regulate expression of Rep78 and Rep68, probably coinciding with the adenovirus major late transcription factor (MTLF) and the two YY1-sites [50] in the AAV p5-promoter.

EXAMPLE 4

Decreased basal level of chloroamphenical acetyltransferase (CAT) expression of a promoter regulated by both a regulatable transactivator and a regulatable transrepressor. Constructs. The constructs pOPI3CAT and pCMVLacI were obtained from Stratagene (La Jolla, California, USA). pCMVLacI contains the E. coli lac repressor under transcriptional control of the CMV promoter. In ptet(o)OPCAT the constitutive Rous Sarcoma Virus (RSV) promoter from pOPI3CAT was exchanged for the tet-operon promoter by ligating the 5.7 kb SnaBI-BglII fragment from pOPI3CAT to a 0.66 kb. PvuII-BamHI fragment containing the tet-operon+minimal TATA-Box from the CMV promoter. The latter fragment was obtained from a pbluescript SK+ (Stratagene, La Jolla, Calif., USA) containing the ClaI-BamHI fragment from pUHD10-3 (obtained from Prof. Bujard) in the ClaI-BamHI sites of pBluescript SK+. The construct pCMVLacZ was used as a transfection efficiency control. It carries the E. coli β-galactosidase gene as a reporter gene under the transcriptional control of a CMV promoter.

A reporter gene (CAT) was used to analyze the activity of a promoter with a regulatable transactivator (tet-VP16) and a regulatable repressor (LacI). The tet-VP16 system has been described in example 1 of this application. The E. coli lac-repressor/operator/inducer system has been shown to function in mammalian cells (Dueschle, U. Hibskind, R.A. and Bujard, H. (1990). Science 248, 480–483). Repression with this system can be obtained via various methods of transcription interference. We used a system, marketed by Stratagene (La Jolla, Calif., USA), in which the transcribing RNA-polymerase II is blocked during elongation by a lac repressor/operator complex. The lac repressor/operator complex can be released from the transcription unit, thus allowing elongation by the addition of isopropyl β-D-thiogalactopyranoside (IPTG) to the culture medium. In ptet(o)OPCAT, expression of CAT can be regulated by adding IPTG and/or tetracycline or its analogs such as doxycycline to the medium. Our presumption was that a promoter containing both a regulatable transrepressor and transactivating function will show less expression in the off-state. In the tet(o)OPCAT plasmid, this situation is created when the tet-VP16 fusion protein is prevented from binding and the lac-repressor is bound to the transcription unit.

To test this presumption, HtTA cells were transiently transfected with the following constructs: pCMVLacI, ptet(o)OPCAT, pBluescript SK+, and pCMVLacZ. Transfections and subsequent culture were performed in DMEM+ 10% FCS and Gentamycin (50 µg/ml). Transfections were performed using the Calcium phosphate transfection system from Life Technologies (Breda, The Netherlands) according to the manufacturers description. HtTA cells (3–6 $10^5$ cells per dish) were seeded into 8 60 mm dishes (Greiner, Alphen aan de Rijn, The Netherlands) one day prior to transfection. The next day, the medium was replaced by medium and, when indicated, doxycycline (1 µg/ml, Sigma) was added. Three hours later, 4 dishes received the Calcium-phosphate precipitate containing 3 µg pCMVLacI, 1 µg pCMVLacZ, 0.3 µg ptet(o)CAT and 2.7 ug pBluescript SK$^+$. The other four dishes served as negative controls and were not transfected. Fourty hours after transfection, IPTG (3 mM) was added to the relevant dishes and approximately 8 hours later the cells were washed with PBS and harvested in 1 ml of fresh PBS by scraping with a rubber policeman. The suspension was transferred to an eppendorf tube and the cells were spun 5 min. at 6000 rpm. The cell pellet was re-suspended in 100 µl 250 mM Tris-HCl (pH 7.8). The cells were lysed by three freeze-thaw cycles and the debri was removed by centrifugation (14 krpm, 5 min., rt). β-galactosidase activity in the extract was measured as described in Sambrook et al (Sambrook J, Fritsch EF, Maniatis T: Molecular Cloning: A laboratory manual. 1989). Samples were diluted in 250 mM Tris-HCl (pH 7.8) so that they contained the same β-galactosidase activity. From the dilutions, 80 µl was used to determine the CAT activity. The CAT-assays were performed as described in (Sambrook J, Fritsch EF, Maniatis T: Molecular Cloning: A laboratory manual. 1989). The thin layer chromatography plates were exposed to photostimulable storage phosphor plates and scanned with a PhosphorImager (Molecular Dynamics, Sunnyvale, Calif.) and chloroamphenicol conversion was quantitated.

Two independent experiments were performed. The results of the experiments are depicted in FIG. 6. The upper part of FIG. 6 shows the autoradiogram of the CAT-assay. Lanes 1 to 4 of exp. 1 and 9 to 12 of exp. 2 shows the CAT-assay from the transfection and lanes 5 to 8, Exp. 1 and 13 to 16, exp. 2 show the result from the untransfected control cultures. Below the autoradiogram is depicted whether IPTG or Doxycycline (Dox.) was present (+) or absent (−) during the experiment. The middle part of FIG. 6 show the percentage conversion of chloroamphenical into acytylatedforms from each lane. The lower part of FIG. 6 shows the induction of CAT-activity in the samples relative to the CAT-activity in the most repressed state (−IPTG, +Dox.) within the same experiment. In the presence of doxycycline and in the absence of IPTG, when the promoter is in its most repressed state, CAT-expression can be detected, albeit at a very low level (FIG. 6A, lane 2 and lane 10). In the absence of doxycycline or the presence of IPTG, when only one of the two regulatable elements is in the off state, CAT-activity is increased by respectively 19 and 2.3-fold. Thus, the combination of a regulatable activator and repressor system within a transcription unit allows more efficient silencing of transcription than when only one regulatable element is present.

LITERATURE CITED

1. Berni, K. I *Microbiol. Rev.* 54, 316–329 (1990).
2. Berns, K. I. in *Virology* (eds. Chanock, R. M., Hirsch, M. S., Melnick, J. L,., Monath, T. P. & Roizman, B.) 1743–1763 (Ravoen Press, New York, 1990).
3. Samiuski, R. J., et al. *EMBO J*. 10, 3941–3950 (1991).
4. Kotin, R. M., et al. *Proc Natl Acad SCI USA* 87, 2211–2215 (1990).
5. Samulski, R. J *Curr Opin Gen Dev* 3, 74–80 (1993).
6. Chejanovsky, N. & Carter, B. J. *Virology* 173, 120–128 (1989).
7. Trempe, J. P. & Carter, B. J. *J of Virol* 62, 3356–3363 (1988).
8. Hermonat, P. L. & Muizyczka, N. *Proc Natl Acad Sci USA* 61, 6466–6470 (1984).
9. Tratschin, J. D., Miller, I. L., Smith, M. G & Carter, B. J. *Mol. Cell Biol.* 5, 3251–3260 (1985).
10. McLaughlin, S. K., Collis, P., Hermonat, P. L. & Muzyczka, N. *J. Viral.* 62, 1963–1973 (1988).
11. Samuliski., R. J., Chang, L. & Shenk, T. *J. Virol.* 63, 3822–3828 (1989).
12. Muzyczka, N. *Curr Top Microbiol Immunol* 158, 97–129 (1992).
13. Valerio, D. in *Transqenic animals* (eds. Grosveld, F. & Kollias, G.) 211–246 (Academic Press, London, 1992).
14. Morgan, R. & Anderson, W. Ann Rev Biochem 63, 191–217 (1993).
15. Miller, A. D., Law, M. F. & Verma, I. M. *Mol. Cell. Biol.* 5, 431–437 (1985).
16. Markowitz, D., Groff, S. & Bank, A. *J. Virology* 167, 400–406 (1988).
17. Markowitz, D., Goff, S. & Bank, A. *J. Virol.* 62, 1120–1124 (1988).
18. Miller, A. D. & Buttimore, C. *Mol. Cell. Biol.* 6, 2895–2902 (1986).
19. Miller, A. D., Trauber, D. R. & Buttimorpe, C. *Somatic Cell. Mol. Genet.* 12, 175–183 (1986).
20. Graham, F. L., Smiley, J., Russell, W. C. & Naiva, R. *J. Gen. Virol.* 36, 59–72 (1997).
21. Miller, A. D., et al. *J of Virol* 65, 2220–2224 (1991).
22. Yang, Q., Chen, F. & Trempe, J. P. *J of Viral* 628 4847–4856 (1994).
23. Holscher C., et al. of *J of Virol* 68, 7169–7177 (1994).
24. Heilbronn, R, Burkie, A., Stephan, S. & zur Hausen, H. *J Viral* 64, 3012–3018 (1990).
25. Tratschin, J. D. Tal, J. & Carter, B. J. *Mol Cell Biol* 6, 2884–2894 (1926).
26. Trempe, J. & Carter, B. *J Viral* 62, 68–74 (1982).

27. Beaton, A., Palumbo P. & Berns, K. *J Virol* 63, 4450–4454 (1989).
28. Hermonat, P. *Cancer Lett* 81, 129–136 (1.994).
29. Bantel-Schaal, U. & zur Hausen, H. *Virology* 164, 64–74 (1988).
30a. Hermonat, P. *Virology* 189, 329–333 (1992).
30b. Clark, K. R., Voulgaropoulou, F., Fraley. D. M., Johnson, P. R. Hum.Gen.Ther. 6, 1329–1341 (1995).
31. Brinster, R. L., Chen, H. Y., Warren, R., Sarthy, A. & Palmiter, R. D. 296 (1982).
32. Mayo, E. K., Warren, R. & Palmiter, R. D. *Cell* 29, 99–108 (1982).
33. Searle, P. F., Stuart, G. W. & Palmiter, R. D. *Mol Cell Biol.* 5, 1480–1489 (1985).
34. Nouer, L. in *Heat Shock Response* (ed. Nouer, L.) (CRC, Boca Raton, Fla. 1991).
35. Hynes, N. E., Kennedy, N., Rahmsdorr, U. & Groner, B. *Proc Natl Acad Sci* 78 2038–2042 (1981).
36. Lee, F., Mulligan, R., Berg, P. & Ringold, G. *Nature* 294, 228–232 (1981).
37. Klock, G., Strahle, U. & Schutz, G. *Nature* 329, 734–736 (1987).
38. S. Israel, D. I. & Kaufman, R. J. *Nucleic Acids Res* 17, 2589–2604 (1989).
39. Lee, S. W., et al. *Proc Natl Acad Sci* 85, 1204–1208 (1988).
40. Brown, M., et. al. *Cell* 49, 603–612 (1987).
41. Hu, M. C. T & Davidson, N. *Cell* 48, 555–566 (1987).
42. Figge, J., Wright, C., Collins, C. J., Roberts, T. M. & Livingston, D. M. *Cell* 52, 713–722 (1988).
43. Deuschle, U., Hipskind, R. A. & Bujard, H. *Science* 248, 480–483 (1990).
44. Labow, M. A., Baim, S. B. Shenk, T. & Levine, A. J. *Mol Cell Biol* 10, 3343–3356 (1990).
45. Baim, S. B. Labow, M. A., Levine, A. J. & Schenk, T. *Proc Natl Acad Sci USA* 88, 5072–5076 (1991).
46. Gatz, C., Kaiser, A. & Wendenburg, R. *Mol Gen Genet* 227, 229–237 (1991).
47. Gossen, M. & Bujard, H. *Proc Natl Acad Sci USA* 89, 5547–5551 (1992).
48. Gossen, M., et al. *Science* 268, 1766–1769 (1995).
49. Einerhand, M., et al. *Gene Ther* 2, 336–343 (1995).
50. Chang, l.-S., Shi, Y. & Shenk, T. *J. Viro* 63, 3479–3488 (1989).

What is claimed is:

1. A recombinant DNA molecule comprising:
   a nucleotide sequence or a gene sequence, wherein said nucleotide sequence or said gene sequence is operably located downstream from a combination of at least one inducible repressor sequence and at least one inducible transactivator sequence wherein the inducible repressor sequence and the inducible transactivator sequence each result in an essentially complete "switch off" state and a "switch on" state for expression of the nucleotide sequence or gene sequence.

2. The recombinant DNA molecule according to claim 1, wherein a product of said gene sequence or nucleotide sequence is toxic for cells expressing said product.

3. The recombinant DNA molecule according to claim 1, wherein said at least one inducible transactivator sequence comprises a binding site for a tetracycline repressor.

4. The recombinant DNA molecule according to claim 1, wherein said at least one inducible repressor sequence comprises a binding site for a YY1 repressor.

5. The recombinant DNA molecule according to claim 1, wherein said at least one inducible repressor comprises a binding site for a major late transcription factor (MTLF).

6. The recombinant DNA molecule according to claim 1, wherein said at least one inducible repressor is derived from an adeno-associated virus p5 promoter.

7. The recombinant DNA molecule according to claim 1, wherein said gene sequence encodes at least a specific part of a Parvovirus protein.

8. The recombinant DNA molecule according to claim 1, wherein said gene sequence is a Parvovirus non-structural gene.

9. A cell comprising a recombinant DNA molecule according to claim 1.

10. A method for an essentially complete switching off of expression of a gene of interest in a host cell, said method comprising:
    growing a host cell comprising a recombinant DNA molecule according to claim 1 under conditions whereby said at least one inducible transactivator and said at least one inducible repressor switch off essentially all expression of said gene of interest.

11. The recombinant DNA molecule according to claim 3 wherein said binding site for a tetracycline repressor is derived from tn10.

---

SEQUENCE LISTING

<160> NUMBER OF SEQ ID NOS: 2

<210> SEQ ID NO 1
<211> LENGTH: 37
<212> TYPE: DNA
<213> ORGANISM: adeno-associated virus 2

<400> SEQUENCE: 1
attaatctag actagtcgcg cagccgccat gccgggg                    37

<210> SEQ ID NO 2
<211> LENGTH: 20
<212> TYPE: DNA
<213> ORGANISM: adeno-associated virus 2

<400> SEQUENCE: 2
tgtggaagta gctctctccc                                       20

12. The recombinant DNA molecule according to claim 8, wherein said gene sequence is an adeno-associated virus rep gene.

13. The cell according to claim 9, wherein said cell is an immortalized cell.

14. The cell according to claim 9, wherein said cell is of mammalian origin.

15. The cell according to claim 9, wherein said cell is capable of induced expression and inducible repression of said gene sequence in said recombinant DNA molecule.

16. A packaging cell line for producing recombinant adeno-associated virus particles, wherein said packaging cell line comprises at least one cell according to claim 9.

17. The cell according to claim 15, wherein said cell is capable of inducible expression and repression of Rep78/Rep68, Rep52/Rep40 and/or VP1/VP2/VP3 of an adeno associated virus.

18. A cell line for producing recombinant adeno-associated virus particles comprising:

a packaging cell line according to claim 16, wherein said packaging cell line has been provided with at least one additional recombinant nucleic acid molecule to be packaged comprising a gene of interest, flanked by adeno-associated virus inverted terminal repeats containing in cis the required sequences for rescue, replication, packaging and integration of a recombinant adeno-associated virus vector.

19. The cell line according to claim 18, whereby sequences necessary for production of virus particles are present in genetic material of said packaging cell line or on an additional recombinant nucleic acid provided to said cell line.

20. A method for obtaining recombinant adeno-associated virus, said method comprising:

culturing a cell line according to claim 18 or 19 in a suitable culture medium and harvesting recombinant adeno-associated virus from said culture whereby recombinant adeno-associated virus is obtained.

* * * * *

UNITED STATES PATENT AND TRADEMARK OFFICE
CERTIFICATE OF CORRECTION

PATENT NO.    : 6,140,103
DATED         : October 13, 2000
INVENTOR(S)   : Markus Peter Wilhelmus Einerhand and Domenico Valerio It is certified that error appears in the above-identified patent and that said Letters Patent is hereby corrected as shown below:

Column 1,
Line 22, delete the period after "PV"

Column 2,
Line 7, change "see1" to -- see $^1$ --

Column 3,
Line 27, change "$^{30}$A" to -- $^{30A}$ --

Column 8,
Line 61, change "ΔpS-rep" to -- Δp5-rep --

Column 9,
Line 19, change "49" to -- $^{49}$ --
Line 66, insert a period after "respectively"

Column 10,
Line 22, change "rep7B" to -- rep78 --

Column 12,
Line 21, change "Berni" to -- Berns --
Line 33, change "Muizyczka" to -- Muzyczka --
Line 34, change "61" to -- 81 --
Line 38, change "*Viral.*" to -- *Virol.* --
Line 39, change "Samuliski" to -- Samulski --
Line 49, change "Groff" to -- Goff --
Line 49, delete "*J.*"
Line 55, change "Buttimorpe" to -- Buttimore --
Line 58, change "(1997)" to -- (1977) --
Line 60, change "*Viral* 628" to -- *Virol* 68 --
Line 63, change "Burkie" to -- Burkle --
Line 64, change "*Viral*" to -- *Virol* --
Line 66, change "(1926)" to -- (1986) --
Line 67, change "*Viral*" to -- *Virol* --
Line 67, change "(1982)" to -- (1988) --

UNITED STATES PATENT AND TRADEMARK OFFICE
CERTIFICATE OF CORRECTION

PATENT NO.    : 6,140,103
DATED         : October 13, 2000
INVENTOR(S)   : Markus Peter Wilhelmus Einerhand and Domenico Valerio It is certified that error appears in the above-identified patent and that said Letters Patent is hereby corrected as shown below:

Column 13,
Line 3, change "(1.994)" to -- (1994) --
Line 43, change "*Viro*" to -- *Virol* --

Signed and Sealed this

Twenty-fifth Day of March, 2003

JAMES E. ROGAN
*Director of the United States Patent and Trademark Office*